(12) United States Patent
Copar et al.

(10) Patent No.: US 7,968,727 B2
(45) Date of Patent: Jun. 28, 2011

(54) SYNTHESIS OF 4-BROMOMETHYL-2'-FORMYLBIPHENYL AND 4-BROMOMETHYL-2'-HYDROXYMETHYLBIPHENYL AND ITS USE IN PREPARATION OF ANGIOTENSIN II ANTAGONISTS

(75) Inventors: Anton Copar, Smartno pri Litiji (SI); Ljubomir Antoncic, Ljubljana (SI); Matej Antoncic, Ljubljana (SI)

(73) Assignee: Lek Pharmaceuticals, D.D., Ljubljana (SI)

( * ) Notice: Subject to any disclaimer, the term of this patent is extended or adjusted under 35 U.S.C. 154(b) by 270 days.

(21) Appl. No.: 11/887,637

(22) PCT Filed: Mar. 30, 2006

(86) PCT No.: PCT/EP2006/002897
§ 371 (c)(1),
(2), (4) Date: Aug. 3, 2009

(87) PCT Pub. No.: WO2006/103068
PCT Pub. Date: Oct. 5, 2006

(65) Prior Publication Data
US 2009/0318521 A1    Dec. 24, 2009

(30) Foreign Application Priority Data
Apr. 1, 2005 (SI) .................................. P200500082

(51) Int. Cl.
*C07D 235/06* (2006.01)
*C07C 255/03* (2006.01)
*C07C 47/54* (2006.01)
*C07C 33/24* (2006.01)

(52) U.S. Cl. ..................... 548/305.4; 558/410; 568/425; 568/807

(58) Field of Classification Search ........................ None
See application file for complete search history.

(56) References Cited

FOREIGN PATENT DOCUMENTS

| | | | |
|---|---|---|---|
| DE | 10314702 A1 | | 10/2004 |
| EP | 0520423 | * | 12/1992 |
| EP | 0520423 A | | 12/1992 |
| EP | 0973729 A | | 1/2000 |

* cited by examiner

*Primary Examiner* — Rebecca L Anderson
*Assistant Examiner* — Alicia L Otton
(74) *Attorney, Agent, or Firm* — Arent Fox LLP

(57) ABSTRACT

4-bromomethyl-2'-formylbiphenyl and 4-bromomethyl-2'-hydroxymethylbiphenyl are useful starting material for the preparation various angiotenzin II antagonists, which are prepared from 4-bromomethyl-2'-cyanobiphenyl or 4'-bromomethylbiphenylcarboxyilic derivatives using selected hydride reagent.

21 Claims, No Drawings

SYNTHESIS OF 4-BROMOMETHYL-2'-FORMYLBIPHENYL AND 4-BROMOMETHYL-2'-HYDROXYMETHYLBIPHENYL AND ITS USE IN PREPARATION OF ANGIOTENSIN II ANTAGONISTS

This application is the National Stage of International Application No. PCT/EP/2006/002897, filed on Mar. 30, 2006, which claims benefit under 35 U.S.C. §119(e) of Slovenia application No. P200500082, filed on Apr. 1, 2005, the contents of both are incorporated herein by reference in their entirety.

FIELD OF THE INVENTION

The present invention relates to the preparation of 4-bromomethyl-2'-formylbiphenyl and 4-bromomethyl-2'-hydroxymethylbiphenyl and their use as intermediates in preparation of angiotensin II antagonists.

BACKGROUND OF THE INVENTION

Biphenylic types of organic compounds in accordance with our invention or which can be prepared from those compounds can be used as a medicament, or more preferably for the manufacture of a medicament for treatment of hypertension and may function as angiotensin II antagonists. Most of molecules from this group consist of cyclic, preferably heterocyclic part connected through —$CH_2$— bridge to the 4-biphenylyl part in which the distant phenyl ring is further orto substituted with a polar substituent. Some well known representatives of this group like losartan, irbesartan, candesartan, olmesartan and valsartan include a tetrazole as a polar substituent while telmisartan includes a carboxylic group in this part of molecule. Also compounds being substituted by other polar substituents, which include oxo or dioxo substituted imidazoles, thiazoles, oxazoles or pyrimidines may be used as a medicament or can be used in the process of manufacturing of a medicament.

2'-substituted (such as tetrazolyl but also formyl and hydroxymethyl) 4-biphenylyl substituted molecules, may be useful angiotenzin II antagonists. Furthermore the enzymes in human body can transform these into a carboxylic moiety. Molecules, which include such fragments are therefore potential prodrugs with improved pharmacokinetics. For instance telmisartan, which has a 2' carboxylic acid substituent, is poorly soluble in water or physiological fluids and there is a tendency to find an (alternative) optimal way to ensure a good bioavailability.

In EP 682021 a 4'-((1,4'-dimethyl-2'-propyl-2,6'-bi(1H-benzo[d]imidazol)-1'-yl)methyl)biphenyl-2-carbaldehyde is used for condensation reaction with thiazolidin-2,4-dion. In EP 520423 various 2-formyl derivatives are used in cyanohydrine reaction in a preparation of 2,4 dioxotiazidinyl substituted compounds. Such formyl derivatives were prepared from corresponding carboxy derivatives of already finished molecular systems by two step procedure, first reducing carboxy group to hydroxymethyl with further oxidation to a formyl derivative. It is more convenient to make a conversion into the formyl group in the early synthetic step.

DISCLOSURE OF INVENTION

The invention provides compounds, their uses and processes where they are prepared, of general formula:

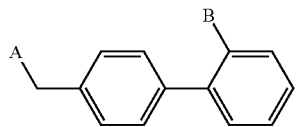

where A is halo, preferably bromo, or cyano, and B is CHO or $CH_2OH$. Preferred compounds are 4-bromomethyl-2'-formylbiphenyl (I) and 4-bromomethyl-2'-hydroxymethylbiphenyl (II).

Above compounds are used for the preparation of various angiotenzin II antagonists, preferably telmisartan.

They are used in a process where said compounds, preferably: 4-halomethyl-2'-formylbiphenyl or 4-halomethyl-2'-hydroxymethylbiphenyl is reacted with another molecule (R) characteristic for the selected target molecule, preferably with an aminoacid, which is preferably N-pentanoylvaline or with a cyclic system containing at least one nitrogen atom, preferably with a heterocyclic system comprising —NH in a cycle, more preferably with a substituted imidazole or benzimidazole on the position 1. The reaction, i.e. condensation is carried out in the presence of at least one base, preferably metal hydroxide, carbonate or alcoholate in an appropriate solvent, preferably polar solvent which can be selected from amides, sulfoxides, sulfones, alcohols, chlorinated hydrocarbons, ketones, nitriles or ethers; preferably in an amide, which is more preferably N,N-dimethylacetamide or in dimethylsulfoxide.

In another aspect, the invention provides in first embodiment a process for preparation of 4-halomethyl-2'-formylbiphenyl from corresponding 4-halomethyl-2'-cyanobiphenyl, in another embodiment a process for preparation of 4-halomethyl-2'-hydroxymethylbiphenyl characterized in that it is prepared from 4'-halomethylbiphenyl-2-carboxylic acid or its derivative, preferably ester, more preferably methyl ester. Most preferably by reduction with an equimolar amount or a molar excess preferably not more than 1.5 to substrate of dibutylaluminium hydride in first embodiment and with molar excess above 2 in second embodiment.

The invention specifically provides an efficient synthesis of 4-bromomethyl-2'-formylbiphenyl (I) from 4-bromomethyl-2'-cyanobiphenyl using a hydride reagent. In a preferred embodiment the preparation is provided using dibutylaluminium hydride in an aprotic solvent in 1.0 to 1.5 molar ratio to the substrate.

In another aspect, the invention provides an efficient synthesis of 4-bromomethyl-2'-hydroxymethylbiphenyl (II) from 4'-bromomethylbiphenyl-2-carboxylic derivatives using a hydride reagent. In a preferred embodiment the preparation is provided using dibutylaluminium hydride in an aprotic solvent in molar ratio above 2 to the substrate.

The invention also provides a process for preparing intermediate of telmisartan wherein 4-bromomethyl-2'-hydroxymethylbiphenyl or 4-bromomethyl-2'-formylbiphenyl is reacted with 2-(1-propyl)-4-methyl-6-(1'-methylbenzimidazol-2-yl)benzimidazole, preferably a process for preparing 4'-[(2-n-propyl-4-methyl-6-(1-methyl-imidazol-4-yl)-benzimidazol-1-yl)methyl]-2-hydroxymethylbiphenyl or 4'-[(2-n-propyl-4-methyl-6-(1-methyl-imidazol-4-yl)-benzimidazol-1-yl)methyl]-2-formylbiphenyl.

Angiotenzin II antagonists with a characteristic carboxy group in the biphenyl part of the molecule, such as telmisartan, are prepared by subsequent oxidation of a formyl or hydroxymethyl group of derivatives, which are prepared when 4-halomethyl-2'-formylbiphenyl or 4-halomethyl-2'- hydroxymethylbiphenyl is reacted with another molecule (R) characteristic for the selected target molecule.

In a specific embodiment a process for preparing telmisartan comprises step of:
a) providing 4-halomethyl-2'-formylbiphenyl or 4-halomethyl-2'-hydroxymethylbiphenyl; b) reacting the compound obtained in previous step with 2-(1-propyl)-4-methyl-6-(1'-methylbenzimidazol-2-yl)benzimidazole; and c) oxidizing the compound obtained in previous step.

In an embodiment 4'-[(2-n-propyl-4-methyl-6-(1-methyl-imidazol-4-yl)-benzimidazol-1-yl)methyl]-biphenyl-2-carboxaldehyde which is obtained in step b) above is oxidized using OXONE® (Aldrich) preferably in N,N-dimethylformamide or using sodium perborate preferably in acetic acid or using sodium chlorate (III) preferably in organic solvent-water mixture or using organic peracid to give 4'-[(2-n-propyl-4-methyl-6-(1-methyl-imidazol-4-yl)-benzimidazol-1-yl)methyl]-biphenyl-2-carboxylic acid known as telmisartan.

In an embodiment 4'-[(2-n-propyl-4-methyl-6-(1-methyl-imidazol-4-yl)-benzimidazol-1-yl)methyl]-2-hydroxymethylbiphenyl which is obtained in step b) above is oxidized with potassium permanganate in alkaline medium or with organic peracids in organic solvents to give 4'-[(2-n-propyl-4-methyl-6-(1-methyl-imidazol-4-yl)-benzimidazol-1-yl)methyl]-biphenyl-2-carboxylic acid.

Preferably 4-halomethyl-2'-formylbiphenyl or 4-halomethyl-2'-hydroxymethylbiphenyl provided in step a) above is obtained from corresponding 4'-halomethylbiphenyl derivative.

Those and other angiotenzin II antagonists with polar cyclic moieties like hydantoins, thiohydantoins, 1,3-oxazol-4-ones, 1,3-oxazol-2,4-diones, 1,3-thiazol-4-ones, 1,3-thiazol-2,4-diones, N,N—($C_1$-$C_4$-dialkyl substituted barbiturates and other 4,6-dioxo substituted pyrimidines bound through —$CH_2$— bridge to the biphenyl part of the molecule are prepared by condensation reaction with corresponding heterocycles and formyl or hydroxymethyl substituted biphenyl containing starting compounds, similar to (I) or (II), where bromomethyl may be replaced with another halomethyl or similar substituent.

Thus a process for preparing an angiotenzin II antagonist comprises following steps: preparing 4-halomethyl-2'-formylbiphenyl by reduction of 4-halomethyl-2'-cyanobiphenyl; or preparing 4-halomethyl-2'-hydroxymethylbiphenyl by reduction of 4-halomethylbiphenyl-2-carboxylic acid or derivative thereof; reacting the compound obtained in previous step with an aminoacid, or with a cyclic system containing at least one nitrogen atom; and oxidizing the compound obtained in previous step; and optionally converting the group oxidized in previous step into a tetrazolyl, or salt thereof.

Preferably halo is bromo, the amino acid is N-pentanoylvaline, and the cyclic system containing at least one nitrogen atom is a substituted imidazole or benzimidazole and preferably the oxidized group is converted into a tetrazolyl, or salt thereof by amidation, conversion to cyano and reaction with an azide.

Said angiotenzin II antagonists may be preferably selected from telmisartan, losartan, irbesartan, candesartan, olmesartan, and valsartan, their salts or esters, which can be used for manufacturing a medicament by incorporating into a pharmaceutical composition.

Specifically the invention is embodied in process for preparing telmisartan characterized by comprising the steps: a) preparing 4-bromoethyl-2'-formylbiphenyl by reduction of 4-bromomethyl-2'-cyanobiphenyl; or preparing 4-bromomethyl-2'-hydroxymethylbiphenyl by reduction of 4-bromoethylbiphenyl-2-carboxylic acid or derivative thereof; b) reacting the compound obtained in previous step with 2-(1-propyl)-4-methyl-6-(1'-methylbenzimidazol-2-yl)benzimidazole; and c) oxidizing the compound obtained in previous step.

Preferably reduction is performed with dibutylaluminium hydride and oxidation is performed with selective oxidizing agent for oxidation of aldehyde or alcohol into acid.

An aspect of the invention is a method of treating a patient in need thereof by administering an angiotenzin II antagonist characterized in that it is prepared by a process in which either 4-halomethyl-2'-formylbiphenyl or 4-halomethyl-2'-hydroxymethylbiphenyl is used.

DETAILED DISCLOSURE OF INVENTION

We have developed a short method of the synthesis of compounds in accordance with our invention, preferably substituted 2'-formyl-4-biphenylylmethyl and 2'-hydroxymethyl-4-biphenylylmethyl and their derivatives which can be used as a medicament, and/or as a prodrug thereof and/or intermediates for their preparation. The invention provides for a simple preparation of 4-bromomethyl-2'-formylbiphenyl (I) and 4-bromomethyl-2'-hydroxymethylbiphenyl (II). We have surprisingly found that they can be prepared in a short simple way from 4-(2-cyanophenyl)toluene (III) but only when reducing agents and reaction order are careful selected.

Namely: if 4-(2-cyanophenyl)toluene is first reduced into 4-(2-formylphenyl)toluene by Raney Ni in formic acid as it is described in J. Chem. Soc., Suppl. 1964 (1), 5880-1, the obtained aldehyde can not be brominated selectively. (Scheme 1).

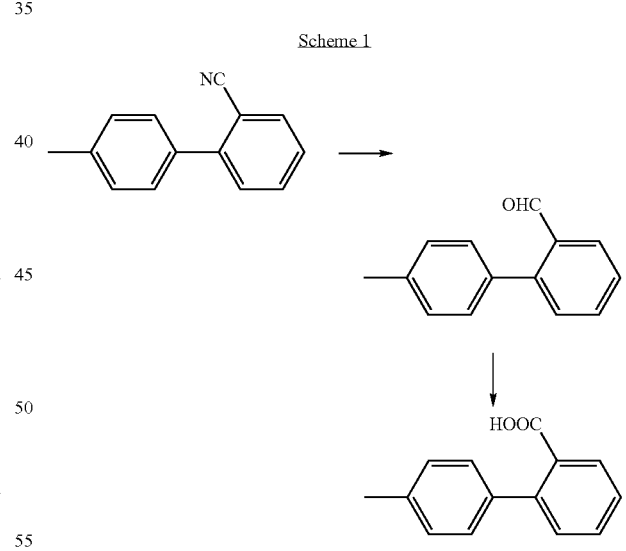

Scheme 1

According to our invention the starting compound (III) could be however firstly halogenated, preferably brominated and subsequently reduced to aldehyde. 4-(2-cyanophenyl)toluene was submitted to bromination with agents such as bromine, pyrrolidone hydrotribromide, 1,3-dibromo-5,5-dimethylhydantoine or N-bromosuccinimide with radical initiators like dibenzoyl peroxide, azoisobutyronitrile to give 4-bromomethyl-2'-cyanobiphenyl (IV). 4-Bromomethyl-2'-cyanobiphenyl (IV) can be reduced with various reducing agent but mainly mixtures are obtained. Raney Ni in formic acid for instance reduce it into 4-(2-formylphenyl)toluene (structure a, Scheme 2), while some others like lithium aluminum hydride give various amounts of aminomethyl derivative (structure b, Scheme 2).

On the other hand we have developed a selective reduction of (IV) into (I) by diisobutylaluminium hydride (DIBALH). Using 1.3 M DIBALH solution in hexane in a careful substrate/DIBALH molar/molar ratio from 1.0 to 1.5, preferably 1.05 to 1.25 it selectively reduces cyano group into aldehyde (Scheme 2).

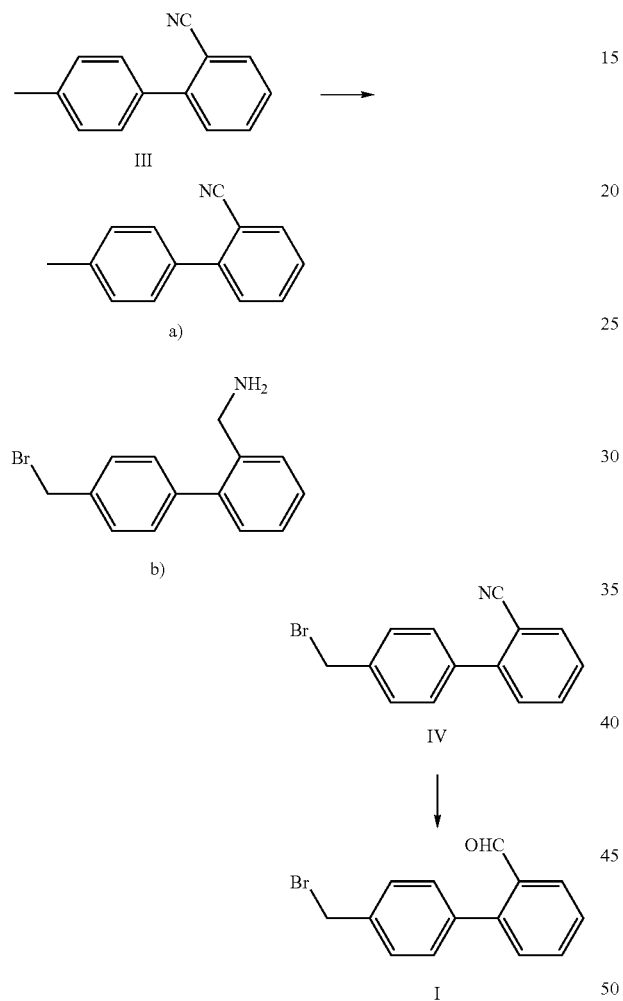

4-Bromomethyl-2'-hydroxymethylbiphenyl (II), another compound of invention, was prepared from 4'-bromomethylbiphenyl-2-carboxylic acid methyl ester by reaction with reducing agent in excess (Scheme 3). The reduction can be accomplished by inorganic or organic metal hydrides like lithium aluminium hydride, dibutylaluminium hydride, metal borohydrides like sodium borohydride alone or with coreagents like metal salts such as lithium, zinc, cobalt and zirconium salts or various boranes and borohydrides alone or in complexes with nitrogen, sulphur, oxygen and phosphorous Lewis bases in anhydrous solvents taken from the group of ethers or aromatic and aliphatic hydrocarbons or mixtures of them. The excess of the reagent can be between 2.0 to 20 mol per mol of substrate, preferably 2.1 mol per mol of substrate. The preferable embodiment comprises a reduction with excess (up to 10%, preferably up to 5% per mol) of dibutylaluminium hydride (20% wt/wt solution) in toluene.

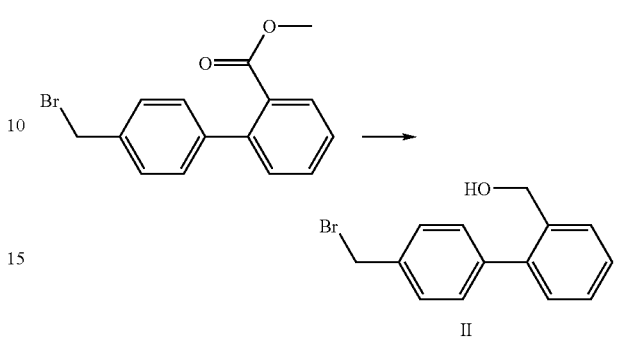

The reaction of reduction is not limited to the reaction on methyl ester of 4'-bromomethylbiphenyl-2-carboxylic acid, but can be applied to other acid derivatives such as various alkyl and aryl ester, to acid halides, anhydrides, unsubstituted and substituted amides, hydrazides and hydroxamic acids of 4'-bromomethylbiphenyl-2-carboxylic acid, and to the acid itself, or salts of those.

In order to prepare various compounds in accordance with our invention 4-bromomethyl-2'-formylbiphenyl or 4-bromomethyl-2'-hydroxymethylbiphenyl is condensed with a moiety comprising nitrogen like an acylated amino acid or oligopeptide preferably N-pentanoylvaline or with a cyclic system containing at least one nitrogen atom, preferably with a heterocyclic system comprisingly —NH in a cycle, more preferably with a substituted imidazole or benzimidazole ring by which the reaction is directed to position 1 (Scheme 4, wherein $R_1$ is a suitable substitutent such as alkyl). The condensation is carried out in a basic medium using bases like metal alkoxides,

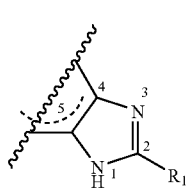

preferably sodium or potassium $C_1$-$C_6$-alkoxides preferably potassium tert-butoxide, alkali or earth alkali hydroxides, preferably sodium or potassium hydroxides, alkali metal carbonates, preferably potassium carbonate, organic nitrogen containing bases like substituted or unsubstituted guanidines preferably DBU (1,8-diazabicyclo[5.4.0]undec-7-ene), or amines characterized with a formula $NR_1R_2R_3$ in which $R_1$ to $R_3$ substituents are same or different linear or branched $C_1$-$C_6$-alkyl in which each two chains can be connected with a bond or 1-3 membered bridge containing C,N,O,S atoms between any of 1-6 position of the chains. The reaction of condensation takes place in a solvent, which may be polar solvents like amides, sulfoxides, sulfones, alcohols, chlorinated hydrocarbons, ketones, nitrites or ethers alone, in mutual mixtures or in mixtures with water. The preferable medium for reaction includes N,N-dimethylformamide or N,N-dimethylacetamide or dimethylsulfoxide or N-methylpyrrolidone or alcohol/water mixture, the most preferable is N,N-dimethylacetamide.

A typical but not limiting example represents a reaction of 2-(1-propyl-4 methyl-6-(1'-methylbenzimidazole-2-yl)benzimidazole with 4-bromomethyl-2'-formylbiphenyl in N,N-dimethylacetamide with potassium tert-butoxide or potassium carbonate or sodium hydroxide as a base to give 4'-[(2-n-propyl-4-methyl-6-(1-methyl-imidazol-4-yl)-benzimidazol-1-yl)methyl]-biphenyl-2-carboxaldehyde. In another typical but not limiting example 4-bromomethyl-2'-formylbiphenyl reacts in similar conditions with 2-butyl-4,4-tetramethylene-4,5-dihydroimidazol-5-one to give 2-butyl-4,5-dihydro-1-((2'-formyl-4-biphenylyl)methyl)-4,4-tetramethyleneimidazol-5-one.

For preparing useful compounds, which may be used as medicament, formyl substitutent on biphenyls of general formula (V) can be transformed into other groups responsible for pharmaceutical effect. The formyl group can be oxidized into a carboxylic group using various oxidative agents selected from the group comprising high oxidation state manganese like manganese (IV) oxide and potassium permanganate, chromium (VI) oxidants like sodium chromate or chromium (VI) oxide adducts, peroxides like hydrogene peroxide in solvents comprising: water, low alkanoic acids or alcohols or mixtures thereof or using oxidative agents selected from the group comprising organic peroxides like alkyl peroxides and carboxylic peroxoacids or higher oxidation state chlorine compounds like metal or organic hypochlorites and sodium chlorate (III) or bromo compounds like bromine, N-bromosuccinimide, inorganic peroxo salts like potassium peroxodisulfate, mixture of $2KHSO_5$,$KHSO_4$,$K_2SO_4$, known under name OXONE® (Aldrich) or sodium perborate or silver oxyde or oxygen under suitable conditions.

Similarly useful angiotenzin II antagonists can be prepared from the corresponding hydroxymethyl substituted biphenyls of general formula (VI). The hydroxymethyl group can be oxidized into a carboxylic group using various oxidative agents like high oxidation state manganese compounds like manganese (IV) oxide and potassium permanganate, chromium (VI) oxidants like sodium chromate or chromium (VI) oxide adducts, peroxides like hydrogene peroxide in water, low alkanoic acids or alcohols or organic peroxides like alkyl peroxides and organic peracids, nitric acid, inorganic peroxo salts like potassium peroxodisulfate, OXONE® (Aldrich) or sodium perborate, silver oxyde or oxygene.

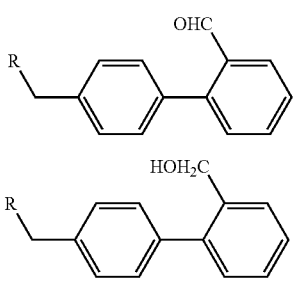

The carboxylic group can be optionally further converted to another substituent, for example into cyano, which can be transformed with an azide into tetrazoyl.

In a characteristic but not limiting example 4'-[(2-n-propyl-4-methyl-6-(1-methyl-imidazol-4-yl)-benzimidazol-1-yl)methyl]-biphenyl-2-carboxaldehyde was oxidized with oxidizing agents like OXONE® (Aldrich) in N,N-dimethylformamide or sodium perborate in acetic acid or sodium chlorate (III) in organic solvent-water mixture to give 4'-[(2-n-propyl-4-methyl-6-(1-methyl-imidazol-4-yl)-benzimidazol-1-yl)methyl]-biphenyl-2-carboxylic acid. (Scheme 5).

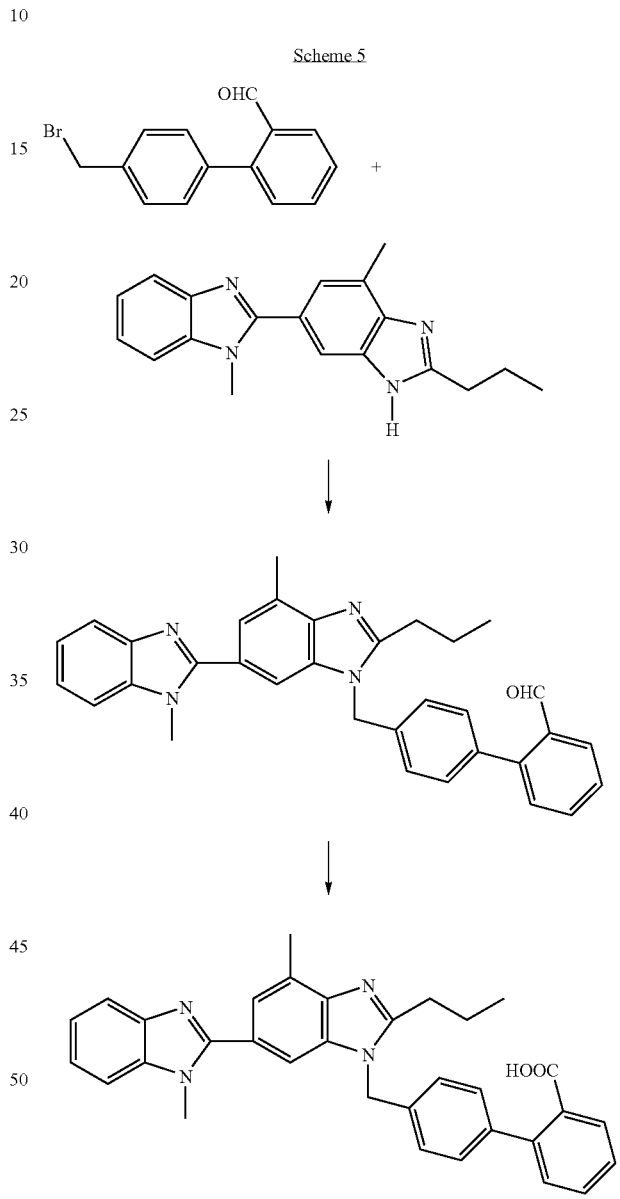

Formyl substituted biphenyls can also be used in condensation reactions with active methylene group in compounds like hydantoins, thiohydantoins, 1,3-oxazol-4-ones, 1,3-oxazol-2,4-diones, 1,3-thiazol-4-ones, 1,3-thiazol-2,4-diones, N,N—($C_1$-$C_4$-dialkyl substituted barbiturates and other 4,6-dioxo substituted pyrimidines in order to obtain potential angiotenzin II antagonists with various polar substituents in the position 2' of biphenyls. For the same reason the corresponding formyl compound can be used in cyanohydrine reaction to obtain α-hydroxy substituted nitrites as important starting materials for further transformation. In a characteristic reaction 2-butyl-4,5-dihydro-1-((2'-formyl-4-biphenylyl)methyl)-4,4-tetramethyleneimidazol-5-one can be condensed with 1,3-thiazolidin-2,4-dione in acetic acid to give 2-butyl-4,5-dihydro-1-((2'-((2,4-dioxo-1,3-thiazol-5-ylidene)methyl)-4-biphenylyl)methyl)-4,4-tetramethyleneimidazol-5-one (Scheme 6).

Scheme 6

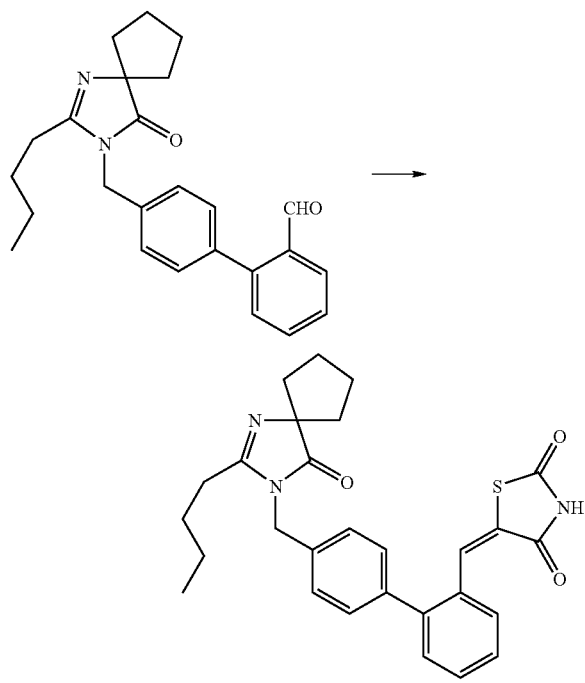

Starting from compounds of general formula (VI) In a characteristic but not limiting example 4'-[(2-n-propyl-4-methyl-6-(1-methylimidazol-4-yl)-benzimidazol-1-yl)methyl]-2-hydroxymethylbiphenyl was oxidized with potassium permanganate in alkali solution to give 4'-[(2-n-propyl-4-methyl-6-(1-methyl-imidazol-4-yl)-benzimidazol-1-yl) methyl]-biphenyl-2-carboxylic acid (telmisartan)—(Scheme 7).

Scheme 7

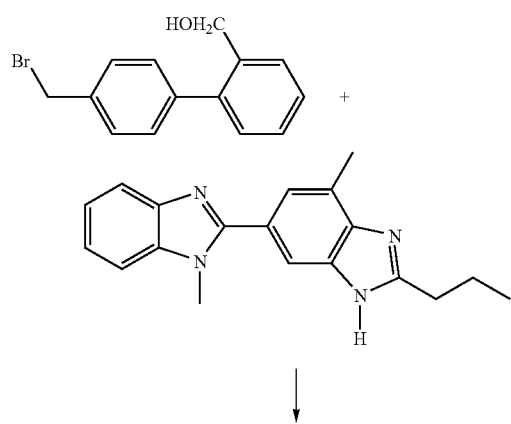

The following examples are intended to illustrate the invention:

Example 1

4-(2-formylphenyl)toluene

To a solution of 10 g (0.051 mol) of 4-(2-cyanophenyl) toluene in 300 ml of formic acid 30 g of Raney Ni is added. Reaction mixture is stirred at the 85° C. overnight and filtered. Filter cake is washed with 50 ml of dichloromethane. 150 ml of water are added to the filtrate, mixture is stirred for 10 minutes and layers separated. Organic layer is dried over $MgSO_4$ and evaporated under reduced pressure giving 7.13 g of oily residue, which is purified on chromatographic column (silica gel, petroleum ether:ether 4:1) to produce 5.23 g of pure product in a form of a brown oil.

$^1$H-NMR (CDCl$_3$): δ 2.45 (s, 3H), 7.44-8.05 (m, 8H), 10.01 (s, 1H). (M+H)$^+$=197.

Example 2

4'-Methylbiphenyl-2-carboxylic acid

A solution of 4-(2-formylphenyl)toluene (2 g, 10.2 mmol), N-bromosuccinimide (1.8 g, 10.1 mmol) and dibenzoyl peroxide 75% (0.26 g, 0.8 mmol) in 22 ml of dichloromethane is stirred at the temperature of reflux for 5 hours. Reaction mixture is filtered and evaporated to dryness under reduced pressure. Oily residue is suspended in 20 ml of brine and extracted with 20 ml of ethyl acetate. Organic layer is evaporated to dryness under reduced pressure to obtain 2.88 g of oily product.

(M+H)$^+$=213.

Example 3

4-Bromomethyl-2'-formylbiphenyl (I)

To a solution of 4-bromomethyl-2'-cyanobiphenyl (IV) (10 g, 37.5 mmol) in 37.5 ml of dichloromethane at a temperature between 0° C. and −5° C. in argon atmosphere, 50 ml of diisobutylaluminium hydride (DIBAL-H) (1M in n-hexane, 50 mmol) are added in a period of 3 hours. Reaction mixture is thereafter poured in a mixture of 200 g of ice and 46 ml of 6 M hydrochloric acid and stirred at room temperature for 1 h. Layers are separated and the aqueous layer is reextracted twice with 50 ml of ethyl acetate. Combined organic layers are washed with 50 ml of 5% solution of NaHCO$_3$ and 50 ml of brine successively. After drying over MgSO$_4$ and evaporating under reduced pressure an oily residue, which crystallizes upon cooling is obtained. Yield: 10.44 g. Mp.: 63-66° C.
$^1$H-NMR (CDCl$_3$): δ 2.48 (s, 2H), 7.35-8.05 (m, 8H), 9.98 (s, 1H). (M+H)$^+$=275.

Example 4

4'-[(2-n-propyl-4-methyl-6-(1-methyl-imidazol-4-yl)-benzimidazol-1-yl)methyl]-biphenyl-2-carboxaldehyde A suspension of 4-bromomethyl-2'-formylbiphenyl (I) (1.0 g, 3.6 mmol), 2-n-propyl-4-methyl-6-(1'-methylbenzimidazol-2-yl)benzimidazole (1.1 g, 3.6 mmol) and NaOH (0.15 g, 3.6 mmol) in 25 ml of N,N-dimethylacetamide is stirred at room temperature under argon atmosphere for 20 hours. Reaction mixture into poured into 160 ml of water and extracted 4 times with 40 ml of ethyl acetate. Combined organic extracts are dried over MgSO$_4$ and evaporated under reduced pressure. Crude amorphous product is obtained in yield: 3.01 g.
$^1$H-NMR (CDCl$_3$): δ 1.06 (t, 3H, J=7.3 Hz), 1.9 (m, 2H, J=7.7 Hz), 2.79 (s, 3H), 2.94 (dd, 2H, J=9.3 Hz, J=7.8 Hz), 3.86 (s, 3H), 5.05 (s, 2H), 7.15-8.02 (m, 14H), 9.92 (s, 1H). (M+H)$^+$=499.

Example 5

4'-[(2-n-propyl-4-methyl-6-(1-methyl-imidazol-4-yl)-benzimidazol-1-yl)methyl]-biphenyl-2-carboxaldehyde A suspension of 4-bromomethyl-2'-formylbiphenyl (I) (1.0 g, 3.6 mmol), 2-n-propyl-4-methyl-6-(1'-methylbenzimidazol-2-yl)benzimidazole (1.1 g, 3.6 mmol) and K$_2$CO$_3$ (0.5 g, 3.6 mmol) in 23 ml of N,N-dimethylacetamide is stirred at room temperature under argon atmosphere for 23 hours. Reaction mixture is poured to 160 ml of water and extracted 4 times with 40 ml of ethyl acetate. Combined organic extracts are dried over MgSO$_4$ and evaporated under reduced pressure to obtain crude amorphous product. Yield: 3.03 g.

Example 6

4'-[(2-n-propyl-4-methyl-6-(1-methyl-imidazol-4-yl)-benzimidazol-1-yl)methyl]-biphenyl-2-carboxaldehyde A suspension of 4-bromomethyl-2'-formylbiphenyl (I) (1.2 g, 4.32 mmol), 2-(1-propyl)-4-methyl-6-(1'-methylbenzimidazol-2-yl)benzimidazole (1.1 g, 3.6 mmol) and potassium tert-butylate (0.41 g, 3.6 mmol) in 25 ml of N,N-dimethylacetamide is stirred at room temperature under argon atmosphere for 5 hours. Reaction mixture is poured in 160 ml of water and stirred for 30 minutes. Obtained precipitated solid is filtered off, suspended in 70 ml of water again, and stirred for 1 hour. Crude product is filtered off and dried in vacuum at 40° C. overnight. Yield: 1.37 g.

Crude product can be recrystallized from 3 ml of ethyl acetate, filtered and washed with 1.5 ml of ethyl acetate. Yield: 740 mg.
Mp: 170-175° C.

Example 7

4'-bromomethyl-2-hydroxymethylbiphenyl (II)

To 60.8 ml (0.0735 mol) of diisobutylaluminium hydride in toluene (20 wt % solution) at 0° C. under argon atmosphere 10.8 g (0.0354 mol) of 4'-bromomethylbiphenyl-2-carboxylic acid methyl ester is added dropwise in a period of 30 minutes. Stirring is continued for 2 hours at the temperature between 0° C. and −5° C. Thereafter 300 ml of 1 M hydrochloric acid and 100 ml of toluene are added under stirring, layers are separated and organic layer washed 3 times with 150 ml of water. After drying with MgSO$_4$ and evaporating under reduced pressure, 9.28 g of white crystalline powder is isolated.
M.p: 101-106° C.
$^1$H-NMR (CDCl$_3$): δ 1.73 (s, 1H), 4.57 (s, 2H), 4.61 (s, 2H), 7.15-7.60 (m, 8H). (M+H)$^+$=277.

Example 8

4'-[(2-n-propyl-4-methyl-6-(1-methyl-imidazol-4-yl)-benzimidazol-1-yl)methyl]-2-hydroxymethylbiphenyl To a mixture of 1.098 g (3.6 mmol) of 2-n-propyl-4-methyl-6-(1'-methylbenzimidazol-2-yl)benzimidazole, 0.41 g of potassium terc-butylate (3.65 mmol) and 15 ml of N,N-dimethylacetamide, a solution of 1 g (3.6 mmol) of 4'-bromomethyl-2-hydroxymethylbiphenyl (II) in 10 ml of N,N-dimethylacetamide is added dropwise at room temperature in 30 minutes. Reaction mixture is stirred at room temperature overnight and subsequently evaporated under reduced pressure to produce 2.69 g of oily residue. Raw product is purified on chromatographic column (silica gel, dichloromethane-methanol 9:1) to yield 1.51 g of pure product in a form of brown oil.
$^1$H-NMR (CDCl$_3$): δ 1.05 (t, 3H, J=7.3 Hz), 1.86 (m, 2H, J=7.6 Hz), 2.76 (s, 3H), 2.93 (t, 2H, J=7.8 Hz), 3.79 (s, 3H), 4.54 (s, 2H), 5.43 (s, 2H), 7.07-7.81 (m, 14H). (M+H)$^+$=501.

Example 9

4'-[(2-n-propyl-4-methyl-6-(1-methyl-imidazol-4-yl)-benzimidazol-1-yl)methyl]-biphenyl-2-carboxylic acid (telmisartan)

A solution of 4'-[(2-n-propyl-4-methyl-6-(1-methylimidazol-4-yl)-benzimidazol-1-yl)methyl)]-biphenyl-2-carboxaldehyde (3.03 g, 6.08 mmol) and OXONE® (3.8 g, 6.18 mmol) in 36 ml of N,N-dimethylformamide is stirred at room temperature for 23 hours and at the temperature of 120° C. for further 4.5 hours, then 50 ml of 1 M hydrochloric acid and 50 ml of ethyl acetate are added. Layers are separated, the water layer is filtered, neutralized with 1 M sodium hydroxide solution and finally evaporated under reduced pressure to yield: 2.5 g.
$^1$H-NMR (CDCl$_3$): δ 1.19 (t, 3H, J=7.3 Hz), 2.04 (m, 2H, J=7.6 Hz), 2.76 (s, 3H), 3.27 (t, 2H, J=7.5 Hz), 3.79 (s, 3H), 5.48 (s, 2H), 7.10-8.41 (m, 14H). (M+H)$^+$=515.

Example 10

4'-[(2-n-propyl-4-methyl-6-(1-methyl-imidazol-4-yl)-benzimidazol-1-yl)methyl]-biphenyl-2-carboxylic acid (telmisartan)

To a solution of 4'-[(2-n-propyl-4-methyl-6-(1-methylimidazol-4-yl)-benzimidazol-1-yl)methyl)]-biphenyl-2-carboxaldehyde (0.5 g, 1 mmol) in 2.5 ml of acetic acid, sodium perborate (0.77 g, 5 mmol) is added in 4 portions in the period of 30 minutes and heated at 100° C. for 3 hours. Another portion of sodium perborate (0.77 g, 5 mmol) and 1 ml of acetic acid is added and heating is continued overnight at the same temperature. Reaction mixture is filtered and poured in 15 ml of water whereupon obtained solid is filtered off and dried. Yield: 0.2 g.

Example 11

4'-[(2-n-propyl-4-methyl-6-(1-methyl-imidazol-4-yl)-benzimidazol-1-yl)methyl]-biphenyl-2-carboxylic acid (telmisartan)

To a suspension of 4'-[(2-n-propyl-4-methyl-6-(1-methylimidazol-4-yl)-benzimidazol-1-yl)methyl]-2-hydroxymethylbiphenyl (0.2 g, 0.4 mmol) in 7 ml of 4 N sodium hydroxide solution, 0.252 g of potassium permanganate (1.5 mmol) is added. Reaction mixture is then stirred overnight at room temperature and finally quenched with 30 ml of saturated solution of $Na_2CO_3$. The obtained mixture is filtered, clear filtrate acidified with acetic acid to pH 4-5 and precipitated solid isolated and dried. Yield: 0.08 g.

Example 12

4'-[(2-n-propyl-4-methyl-6-(1-methyl-imidazol-4-yl)-benzimidazol-1-yl)methyl]-biphenyl-2-carboxylic acid (telmisartan)

A solution of 1.7 g (14.7 mmol) of $NaClO_2 \cdot 4H_2O$ (79% purity) in 7 ml of water is added dropwise to a stirred mixture of 4'-[(2-n-propyl-4-methyl-6-(1-methyl-imidazol-4-yl)-benzimidazol-1-yl)methyl]-biphenyl-2-carboxaldehyde (2.5 g, 4.5 mmol) in 10 ml of acetonitrile, 0.16 g of $NaH_2PO_4$ in 2 ml of $H_2O$ and 2.5 ml of 30% $H_2O_2$ at the temperature 10° C. pH of the mixture is adjusted to pH=2 with concentrated HCl and stirring is continued for 1.5 h at room temperature. Reaction mixture is poured into 120 ml of water, stirred for 15 minutes, filtered, washed with 2×10 ml of water and dried in vacuo. Yield: 2.34 g (90.6%)

Example 13

2-butyl-4,5-dihydro-1-((2'-formyl-4-biphenylyl)methyl)-4,4-tetramethyleneimidazol-5-one A suspension of 4-bromomethyl-2'-formylbiphenyl (I) (1.6 g, 5.8 mmol), 2-butyl-4,4-tetramethyleneimidazol-5-one hydrochloride (1.35 g, 5.85 mmol) and powdered sodium hydroxide (0.55 g, 13.75 mmol) in 14 ml of N,N-dimethylacetamide is stirred at room temperature for 4 hours. Reaction mixture is poured in 28 ml of water and filtered off. Residue is purified on chromatographic column (silica gel, ethyl acetate n-hexane 1:1) to produce 0.64 g of pure product in a form of colorless oil.

$^1$H-NMR ($CDCl_3$): δ 0.87 (t, 3H, J=7.3 Hz), 1.33 (m, 2H), 1.60 (t, 2H, J=7.8 Hz), 1.82-2.05 (m, 8H), 2.36 (t, 2H, J=7.8 Hz), 4.6 (s, 2H), 7.25-8.03 (m, 8H), 9.95 (s, 1H). $(M+H)^+$= 389.

Example 14

2-butyl-4,5-dihydro-1-((2'-formyl-4-biphenylyl)methyl)-4,4-tetramethyleneimidazol-5-one A solution of 4-bromomethyl-2'-formylbiphenyl (I) (2.2 g, 7.9 mmol) in 23 ml of N,N-dimethylacetamide is added to a suspension of 2-butyl-4,4-tetramethyleneimidazol-5-one hydrochloride (1.8 g, 7.8 mmol) and potassium tert. butoxide (1.8 g, 16 mmol) in 32 ml of N,N-dimethylacetamide at room temperature in an inert atmosphere and stirred at room temperature overnight. Reaction mixture is poured in 350 ml of water and extracted 4 times with 90 ml of ethyl acetate. Combined organic layers are dried over $MgSO_4$ and evaporated under reduced pressure. Product is obtained in a form of colorless oily residue. Yield: 6.7 g

Example 15

2-butyl-4,5-dihydro-1-((2'-((2,4-dioxo-1,3-thiazol-5-ylidene)methyl)-4-biphenylyl)methyl)-4,4-tetramethyleneimidazol-5-one 1.4 g 2-butyl-4,5-dihydro-1-((2'-formyl-4-biphenylyl)methyl)-4,4-tetramethylene-imidazol-5-one is dissolved in 15 ml of glacial acetic acid, heated to 120° C. with 0.62 g of thiazolidin-2,4-dione and stirred for 12 hours at this temperature. After evaporation, the mixture is chromatographed on silicagel with ethylacetate/ethanol (1:1) to obtain 0.27 g of final product.

Melting point: 155-166° C. NMR: $^1$H-NMR ($CDCl_3$): δ 0.87 (t, 3H, J=7.3 Hz), 1.36 (m, 2H), 1.62 (t, 2H, J=7.8 Hz), 1.92-2.07 (m, 8H), 2.45 (t, 2H, J=7.8 Hz), 4.77 (s, 2H), 7.21-7.72 (m, 10H). $(M+H)^+$: 488

The invention claimed is:

1. A compound of general formula:

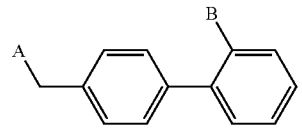

where A is bromo or cyano, and B is CHO or $CH_2OH$.

2. A compound according to claim 1, which is 4-bromomethyl-2'-formylbiphenyl or 4-bromomethyl-2'-hydroxymethylbiphenyl.

3. A method of making an angiotensin II antagonist, which is selected from the group consisting of telmisartan, losartan, irbesartan, candesartan, olmesartan, or valsartan, and salts or esters thereof, comprising reacting the compound of general formula:

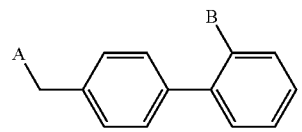

where A is bromo or cyano, and B is CHO or $CH_2OH$, with substituted imidazole or benzimidazole in the position 1 as indicated in the below formula:

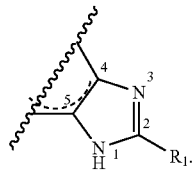

4. The method according to claim 3, wherein the reaction is carried out in at least one polar solvent in the presence of at least one base.

5. The method according to claim 4, wherein the polar solvent is an amide.

6. The method according to claim 4, wherein the polar solvent is N,N-dimethylacetamide.

7. The according to claim 4, wherein the polar solvent is dimethylsulfoxide.

8. The method according to claim 3 wherein the compound of the general formula is 4-bromomethyl-2'-formylbiphenyl or 4-bromomethyl-2'-hydroxymethylbiphenyl and the antiotensin II antagonist is telmisartan.

9. A process for preparation of a 4-halomethyl-2'-formylbiphenyl characterized in that it is prepared from the corresponding 4-halomethyl-2'-cyanobiphenyl by reduction with an equimolar amount or an excess of dibutylaluminium hydride.

10. A process for the preparation of a 4-halomethyl-2'-hydroxymethylbiphenyl characterized in that it is prepared from the corresponding 4'-halomethylbiphenyl-2-carboxylic acid or an ester thereof by reduction with excess amount of dibutylaluminium hydride.

11. The process according to claim 10 wherein the corresponding 4'-halomethylbiphenyl-2-carboxylic acid is the methyl ester of 4'-halomethylbiphenyl-2-carboxylic acid.

12. A process for preparing an intermediate of telmisartan, which is 4'-[(2-n-propyl-4-methyl-6-(1-methyl-imidazol-4-yl)-benzimidazol-1-yl)methyl]-2-hydroxymethylbiphenyl or 4'-[(2-n-propyl-4-methyl-6-(1-methyl-imidazol-4-yl)-benzimidazol-1-yl)methyl]-2-formylbiphenyl, wherein 4-bromomethyl-2'-hydroxymethylbiphenyl or 4-bromomethyl-2'-formylbiphenyl is reacted with 2-(1-propyl)-4-methyl-6-(1'-methylbenzimidazol-2-yl)benzimidazole.

13. A process for preparing telmisartan comprising the following steps:
a) providing 4-halomethyl-2'-formylbiphenyl or 4-halomethyl-2'-hydroxymethylbiphenyl;
b) reacting the compound obtained in previous step with 2-(1-propyl)-4-methyl-6-(1'-methylbenzimidazol-2-yl)benzimidazole; and
c) oxidizing the compound obtained in previous step.

14. The process according to claim 13, wherein 4-halomethyl-2'-formylbiphenyl is employed in step a) and oxidation in step c) is carried out with a reagent selected from the group consisting of a mixture of 2KHSO₅ and KHSO₄ and K₂SO₄, an organic peracid, sodium chlorate and sodium perborate.

15. A process according to claim 13, wherein 4-halomethyl-2'-hydroxymethylbiphenyl is employed in step a), and the oxidation is carried out with a reagent selected from the group consisting of potassium permanganate and carboxylic peracid.

16. A process for preparing telmisartan comprising the following steps:
a) providing 4-halomethyl-2'-formylbiphenyl or 4-halomethyl-2'-hydroxymethylbiphenyl;
b) reacting the compound obtained in previous step with 2-(1-propyl)-4-methyl-6-(1'-methylbenzimidazol-2-yl)benzimidazole; and
c) oxidizing the compound obtained in previous step,
wherein 4-halomethyl-2'-formylbiphenyl is obtained as described in claim 9.

17. A process for preparing telmisartan comprising the following steps:
a) providing 4-halomethyl-2'-formylbiphenyl or 4-halomethyl-2'-hydroxymethylbiphenyl;
b) reacting the compound obtained in previous step with 2-(1-propyl)-4-methyl-6-(1'-methylbenzimidazol-2-yl)benzimidazole; and
c) oxidizing the compound obtained in previous step,
wherein 4-halomethyl-2'-hydroxymethylbiphenyl is obtained as described in claim 10.

18. A process for preparing an angiotensin II antagonist, which is selected from the group consisting of telmisartan, losartan, irbesartan, candesartan, olmesartan, or valsartan, and salts or esters thereof the process comprising the following steps:
a) preparing 4-halomethyl-2'-formylbiphenyl by reduction of 4-halomethyl-2'-cyanobiphenyl; or preparing 4-halomethyl-2'-hydroxymethylbiphenyl by reduction of 4-halomethylbiphenyl-2-carboxylic acid or an ester thereof;
b) reacting the compound obtained in previous step with an amino acid, or with a cyclic system containing at least one nitrogen atom, which is a substituted imidazole or benzimidazole; and
c) oxidizing the compound obtained in previous step; and
d) optionally converting the group oxidized in previous step into a tetrazolyl, or salt thereof.

19. A process according to claim 18, wherein halo is bromo.

20. A process according to claim 18, wherein the amino acid is N-pentanoylvaline.

21. A process according to claim 18, wherein in step d) the group oxidized in the previous step is converted into a tetrazolyl, or salt thereof by amidation, conversion to cyano and reaction with an azide.

* * * * *